US006850586B2

(12) United States Patent
Cahill

(10) Patent No.: US 6,850,586 B2
(45) Date of Patent: Feb. 1, 2005

(54) METHOD AND SYSTEM FOR RECONSTRUCTING AN IMAGE FROM PROJECTION DATA ACQUIRED BY A CONE BEAM COMPUTED TOMOGRAPHY SYSTEM

(75) Inventor: Nathan D. Cahill, West Henrietta, NY (US)

(73) Assignee: Eastman Kodak Company, Rochester, NY (US)

(*) Notice: Subject to any disclaimer, the term of this patent is extended or adjusted under 35 U.S.C. 154(b) by 0 days.

(21) Appl. No.: 10/797,980

(22) Filed: Mar. 11, 2004

(65) Prior Publication Data

US 2004/0170248 A1 Sep. 2, 2004

Related U.S. Application Data

(63) Continuation of application No. 10/255,539, filed on Sep. 26, 2002.
(51) Int. Cl.$^7$ .................................................. A61B 6/03
(52) U.S. Cl. ..................................... 378/8; 3789/901
(58) Field of Search ........................... 378/4, 8, 15, 19, 378/901

(56) References Cited

U.S. PATENT DOCUMENTS

| | | | | |
|---|---|---|---|---|
| 5,270,926 A | | 12/1993 | Tam ................................ | 378/4 |
| 6,009,142 A | | 12/1999 | Sauer et al. .................... | 378/15 |
| 6,130,930 A | | 10/2000 | Tam ................................ | 378/4 |
| 6,233,303 B1 | | 5/2001 | Tam ................................ | 378/4 |
| 6,292,525 B1 | | 9/2001 | Tam ................................ | 378/4 |
| 6,324,243 B1 | | 11/2001 | Edic et al. ...................... | 378/4 |
| 6,463,116 B1 | * | 10/2002 | Oikawa ........................... | 378/4 |
| 6,643,351 B2 | * | 11/2003 | Morita et al. ................... | 378/4 |

OTHER PUBLICATIONS

"Practical Cone–beam Algorithm", by L.A. Feldkamp, L.C. David, and J.W. Kress, J. Opt. Soc. AM A/vol. 1, No. 6, Jun. 1994, pp. 612–619.
"Volumetric Description of Objects from Multiple Views", by Worhty N. Martin and J.K. Aggarwal, IEEE Transactions on Pattern Analysis and Machine Intelligence, vol. PAM1–5, No. 2, Mar. 1983, pp. 150–162.
The Visual Hull Concept for Silhouette–Based Imaged Understanding, by Aldo Laurentini, IEEE Transaction on Pattern Analysis and Machine Intelligence, vol. 16, No. 2, Feb. 1994, pp 150–162.
"Imaging Processing Techniques for Tumor Detection", robin N. Strickland, ed Marcel Deckker, Inc. NY 2002.
"Computer–Aided Diagnosis in Check Radiography" PhD Thesis, University Medical Center Utrecht, 2001, B. van Ginnekin.

* cited by examiner

Primary Examiner—David V Bruce
(74) Attorney, Agent, or Firm—Susan L. Parulski

(57) ABSTRACT

A method and system for reconstructing a three-dimensional image of an object from cone beam projection data. The method comprising the steps of: acquiring the projection data, wherein the projection data comprises a set of cone beam projection images; selecting at least one cone beam projection image; identifying a region of interest within each selected cone beam projection image; defining a three-dimensional lattice of points, wherein the projection into each selected cone beam projection image of the points in the three-dimensional lattice provides a sampling of the identified region of interest in the corresponding selected cone beam projection image; and, reconstructing an image of the object at each point in the three-dimensional lattice to form a three-dimensional image of the object.

9 Claims, 6 Drawing Sheets

METHOD AND SYSTEM FOR RECONSTRUCTING AN IMAGE FROM PROJECTION DATA ACQUIRED BY A CONE BEAM COMPUTED TOMOGRAPHY SYSTEM

CROSS REFERENCE TO RELATED APPLICATION

This is a Continuation of commonly assigned (U.S. Ser. No. 10/255,539), entitled "METHOD AND SYSTEM FOR RECONSTRUCTING AN IMAGE FROM PROJECTION DATA ACQUIRED BY A CONE BEAM COMPUTED TOMOGRAPHY SYSTEM", filed on Sep. 26, 2002 in the name of Cahill, and which is assigned to the assignee of this application.

FIELD OF THE INVENTION

The invention relates generally to the field of three-dimensional (3D) computerized tomography (CT). More specifically, the invention relates to image reconstruction in a cone beam computed tomography imaging system having a radiation source scan path that encircles a region of interest (ROI) in an object.

BACKGROUND OF THE INVENTION

In conventional computerized tomography for both medical and industrial application, an x-ray fan beam source and a linear array detector are employed to achieve a two-dimensional (2D) image. With such an arrangement, only a single slice of an object is imaged at a time. When a 3D image is required, a "stack of slices" approach is employed, which can be inherently tedious and time-consuming.

Another approach, based on "cone beam geometry", employs a cone beam x-ray source instead of an x-ray fan beam source and a two-dimensional array detector instead of a linear array detector. At an instant, the entire object is irradiated by a cone beam x-ray source, and therefore cone beam scanning is faster than slice-by-slice scanning using a fan beam or a parallel beam. To achieve cone beam projection data, an object is scanned, preferably over a 360 degree angular range, either by moving the x-ray source in an appropriate scanning trajectory, for example, a circular trajectory around the object while keeping the 2D array detector fixed with reference to the source, or by rotating the object while the source and detector remain stationary. In either arrangement, it is the relative movement between the source and the object which effects scanning. Image reconstruction is then accomplished in accordance with known techniques.

Direct reconstruction of x-ray attenuation coefficients or "densities" on a 3D mesh of points from 2D x-ray projection data is the basis of modern medical tomographic imaging. Currently, there are a number of commercially available X-ray systems that generate 3D images by means of computed tomography (CT). Typically in these systems, the patient is placed on an examination table, which is transparent to x-rays, and is positioned in the center of a large cylinder-shaped device such that the axis of the patient is aligned with the axis of the cylinder. Within the walls of the cylinder, a source-detector pair, formed by an x-ray point source and a linear detector array, is positioned such that the point source and the center of the detector array are diametrically opposed. The x-ray point source emits a fan-beam radiation pattern in a plane perpendicular to the axis of the cylinder. The detectors in the array are arranged linearly along the arc of a circle whose center is the point source. The detector array is positioned in the plane of the fan-beam and is wide enough to intercept the extreme rays of the fan. In the simplest arrangement, 2D projection data are obtained in the following way. The patient is exposed with the source-detector pair in an initial orientation to obtain an equiangular fan-beam projection. The source-detector pair is then rigidly rotated by an incremental angle about the cylinder axis and another equiangular fan projection is taken. The process is repeated until projection images have been obtained over a full 360°. Then, either the patient or the source-detector pair is advanced an incremental distance along the axis of the cylinder, and another series of fan projections over 360° are obtained. This process is repeated until the desired 2D x-ray projection data is accumulated. Reconstruction of a 2D density distribution within a slice through the patient can be computed from each series of fan-beam projections over 360° (three hundred sixty degrees). Finally, a complete 3D representation of the x-ray density function, $\rho(x,y,z)$, is obtained by combining the individual 2D distributions.

There are several disadvantages to CT systems such as the one described above. For example, the accumulation of 2D projection images is a relatively slow process resulting in prolonged exposure of the patient to X-ray radiation. This results directly from the 360° fan-beam scans, which must be repeated for different positions along the cylinder axis. This is not a desirable situation since, for a given detector sensitivity, the total dosage received by the patient is increased in proportion to the number of cross-sectional scans. Another disadvantage is that such CT systems tend to be very expensive due largely to the cost of manufacturing mechanical assemblies that permit the rapid and precise translation of the source-detector pair relative to the patient. Further, such CT systems tend to be somewhat inflexible; that is, they are typically designed for specific modalities (e.g., chest, stomach, and full body x-rays).

Reconstruction of 3D density distributions from cone-beam projection images represents an alternative method for CT that overcomes many of the disadvantages disclosed above. An x-ray point source emits radiation in a cone, which is intercepted by a 2D detector array. The source-detector pair rotates rigidly about a vertical z-axis, which is aligned to the axis of the patient. Cone-beam projection images are then taken for each discrete angle of rotation over the entire angular range of 360°. The line integral of the x-ray density distribution function along the path from the point source to a location in the detector plane for a particular projection angle is related to the x-ray intensity measured at the corresponding location in the detector array for the particular projection angle 3D cone beam CT systems generally enable diagnostic procedures to be performed more quickly than with other types of CT scanning. In such CT systems that utilize 2D detectors, it is possible to reconstruct spatial volume data at extremely high resolution. In some cases, the resolution may be an order of magnitude higher than the resolution obtained with other types of detectors.

However, manipulating data at this higher resolution is generally prohibitive due to the long reconstruction times and the physical size of the reconstructed volume. High resolution 2D detectors have such a large number of pixels that the amount of data collected is extremely large, which presents problems in terms of storing, retrieving, and manipulating the data in real time. U.S. Pat. No. 6,324,243 (Edic) describes a method and apparatus for use in volumetric CT scanning systems that attempts to reduce the amount of data that is used by initially performing 3D reconstruction on projection images that have been sampled at a lower resolution, and then uses all of the acquired data associated with a particular region of interest to reconstruct a high resolution image of the region of interest. The intermediate step of performing a low resolution 3D reconstruction, while clearly having an advantage over performing a high resolution 3D reconstruction of the entire object, still requires extra computation than is necessary if the region of interest can be identified within one or more of the projection images.

U.S. Pat. No. 6,009,142 (Sauer) describes a technique for reconstructing a region of interest (ROI) in an object when the cone-beam source travels in a helical pattern around the object. Sauer's technique attempts to reduce the computation required for reconstruction by only reconstructing to a region of interest. However, Sauer's technique is not amenable for reconstructing arbitrary regions of interest. Rather, Sauer's region of interest is formed by limiting the object by planes passing through the longitudinal axis of the helix. This prohibits Sauer's technique from being used to reconstruct, for example, a small region around a tumor, if no part of the region intersects the longitudinal axis of the helix.

Accordingly, a need exists for a method and apparatus for use in a 3D cone beam CT system that enables an arbitrary region of interest to be identified in one or more of the cone beam projection images, and provides for the generation of a high resolution 3D reconstruction of the particular region of interest.

SUMMARY OF THE INVENTION

An object of the present invention is to provide a method and apparatus for use in a 3D cone beam CT system that enables an arbitrary region of interest to be identified in one or more of the cone beam projection images, and provides for the generation of a high resolution 3D reconstruction of the particular region of interest.

This object is given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for reconstructing a three-dimensional image of a region of interest of an object disposed within an object region from cone beam projection data. The method comprises the steps of: acquiring the cone beam projection data, the cone beam projection data comprising a plurality of cone beam projection images; identifying a region of interest within each of two projection images; projecting each identified region of interest through at least a portion of the object region to identify a three-dimensional reconstruction region defined by a plurality of points; and reconstructing the image at each of the plurality of points to form the three-dimensional image of the region of interest.

According to another aspect of the invention, there is provided a method for reconstructing a three-dimensional image of a region of interest of an object from cone beam projection data. The method comprises the steps of: acquiring the cone beam projection data, the cone beam projection data comprising a plurality of cone beam projection images; identifying a region of interest within a plurality of projection images; projecting each identified region of interest to a source position corresponding with the associated projection image to define a three-dimensional projected cone; sampling the intersection of the projected cones to determine a three-dimensional reconstruction region defined by a plurality of points; and reconstructing the region of interest at each of the plurality of points to form the three-dimensional image of the region of interest.

According to a further aspect of the invention, there is provided a method for reconstructing a three-dimensional image of a region of interest of an object disposed within an object region from cone beam projection data. The method comprises the steps of: acquiring the cone beam projection data, the cone beam projection data comprising a plurality of cone beam projection images; identifying a region of interest within one of the plurality of projection images; projecting the identified region of interest through at least a portion of the object region to define a three-dimensional reconstruction region defined by a plurality of points; and reconstructing the region of interest at each of the plurality of points to form the three-dimensional image of the region of interest.

According to a still further aspect of the invention, there is provided a method for reconstructing a three-dimensional image of a region of interest of an object from cone beam projection data. The method comprises the steps of: acquiring the cone beam projection data, the cone beam projection data comprising a plurality of cone beam projection images; identifying a region of interest within a first one of the plurality of projection images; projecting the identified region of interest to a source position corresponding with the first one of the plurality of projection images to define a first three-dimensional projection cone; projecting a second one of the plurality of projection images to a source position corresponding with the second one of the plurality of projection images to define a second three-dimensional projection cone; using the first and second projected cones to determine a three-dimensional reconstruction region defined by a plurality of points; and reconstructing the region of interest at each of the plurality of points to form the three-dimensional image of the region of interest.

According to yet another aspect of the invention, there is provided a system for reconstructing a three-dimensional image of a region of interest of an object disposed within an object region from cone beam projection data. The system comprises: means for acquiring the cone beam projection data, the cone beam projection data comprising a plurality of cone beam projection images; means for identifying a region of interest within each of two projection images; means for projecting each identified region of interest through at least a portion of the object region to identify a three-dimensional reconstruction region defined by a plurality of points; and means for reconstructing the image at each of the plurality of points to form the three-dimensional image of the region of interest.

According to another aspect of the invention, there is provided a system for reconstructing a three-dimensional image of a region of interest of an object from cone beam projection data. The system comprises: means for acquiring the cone beam projection data, the cone beam projection data comprising a plurality of cone beam projection images; means for identifying a region of interest within a plurality of projection images; means for projecting each identified region of interest to a source position corresponding with the associated projection image to define a three-dimensional projected cone; means for sampling the intersection of the projected cones to determine a three-dimensional reconstruction region defined by a plurality of points; and means for reconstructing the region of interest at each of the plurality of points to form the three-dimensional image of the region of interest.

According to a further aspect of the invention, there is provided a system for reconstructing a three-dimensional image of a region of interest of an object disposed within an object region from cone beam projection data. The system comprises: means for acquiring the cone beam projection data, the cone beam projection data comprising a plurality of cone beam projection images; means for identifying a region of interest within one of the plurality of projection images; means for projecting the identified region of interest through at least a portion of the object region to define a three-dimensional reconstruction region defined by a plurality of points; and means for reconstructing the region of interest at each of the plurality of points to form the three-dimensional image of the region of interest.

According to a still further aspect of the invention, there is provided a system for reconstructing a three-dimensional image of a region of interest of an object from cone beam projection data. The system comprises: means for acquiring the cone beam projection data, the cone beam projection data comprising a plurality of cone beam projection images; identifying a region of interest within a first one of the plurality of projection images; means for projecting the identified region of interest to a source position corresponding with the first one of the plurality of projection images to define a first three-dimensional projection cone; means for projecting a second one of the plurality of projection images to a source position corresponding with the second one of the plurality of projection images to define a second three-dimensional projection cone; means for using the first and second projected cones to determine a three-dimensional reconstruction region defined by a plurality of points; and means for reconstructing the region of interest at each of the plurality of points to form the three-dimensional image of the region of interest.

BRIEF DESCRIPTION OF THE DRAWINGS

The foregoing and other objects, features, and advantages of the invention will be apparent from the following more particular description of the preferred embodiments of the invention, as illustrated in the accompanying drawings.

DETAILED DESCRIPTION OF THE INVENTION

Figure 1:
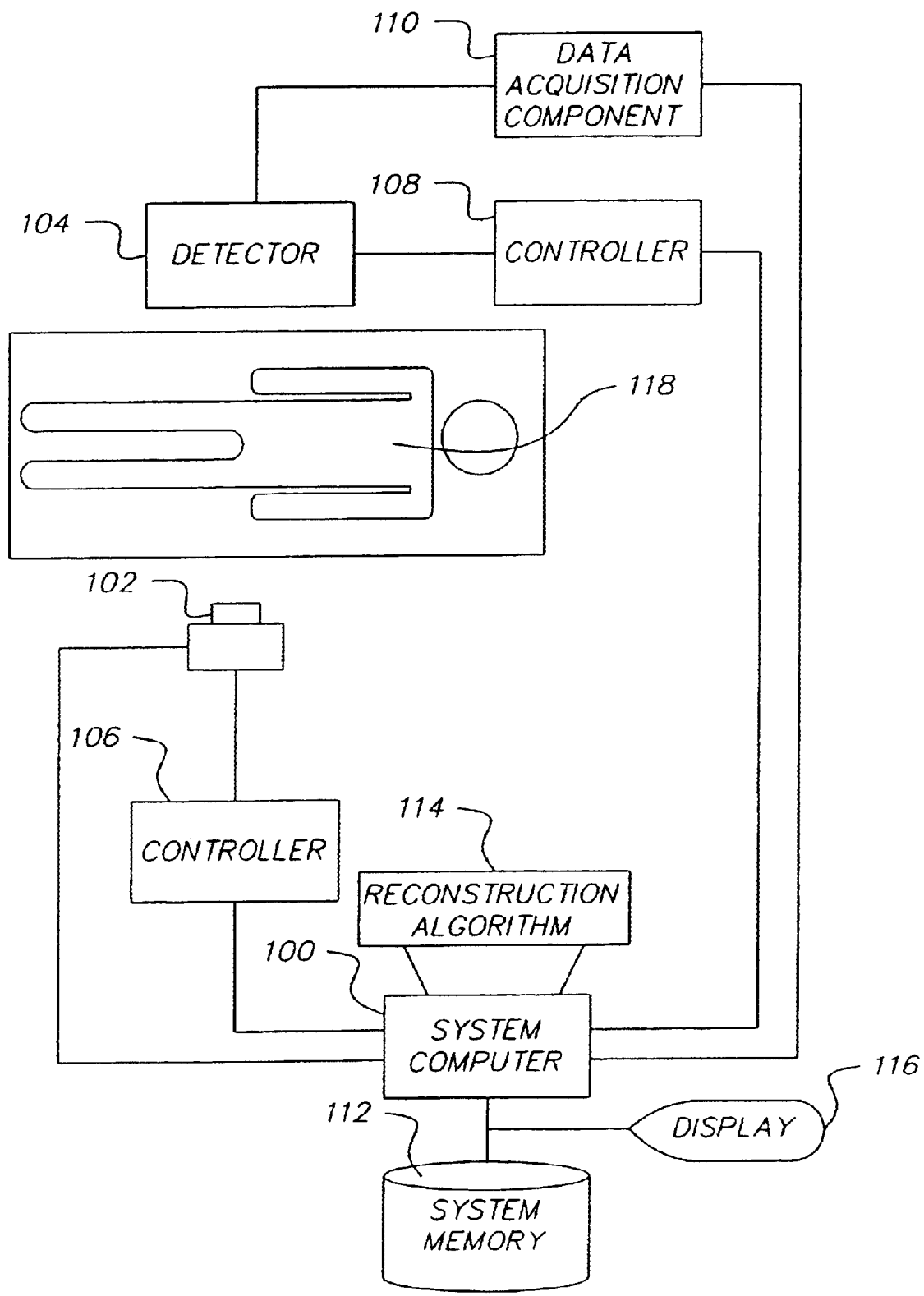
FIG. 1 shows a cone beam CT system suitable for implementing the method of the present invention.

The following is a detailed description of the preferred embodiments of the invention, reference being made to the drawings in which the same reference numerals identify the same elements of structure in each of the several figures.

FIG. 1 shows a diagram of a cone beam CT system in accordance with the present invention which is suitable for implementing the method of the present invention. For ease of convenience and for illustrative purposes only, the cone beam CT system of the present invention will be discussed with respect to reconstructing an image of an anatomical feature of a patient. However, it is understood that the present invention is not limited to the imaging of an individual, nor is the present invention limited to the imaging of any particular object. For example, those skilled in the art will recognize that the present invention can be employed for industrial processes.

In a cone beam CT system, it is known to employ a gantry or other spanning framework for acquiring cone beam projection images. When employing a gantry, the gantry can be rotated about an object disposed within an object region (such as a human patient disposed on a bed) to acquire the projection data. A processor or cone beam CT system computer 100 controls the operations of the cone beam CT system. When referring herein to the rotation of the gantry, it is intended to denote rotation of an x-ray source 102 and/or rotation of a detector 104, which preferably is a high resolution area detector. Accordingly, the gantry can comprise x-ray source 102 and detector 104. Controllers 106 and 108 are controlled by cone beam CT system computer 100 and are illustrated in FIG. 1 as being coupled, respectively, to x-ray source 102 and detector 104. Controllers 106 and 108 cause the appropriate relative rotational motion to be imparted to x-ray source 102 and/or to detector 104 to acquire cone beam projection data. Individual controllers are not necessary; a single controller component can be employed to rotate the gantry.

Computer 100 controls the data acquisition process by instructing a data acquisition component 110 as to when to sample detector 104. Detector 104 is comprised of an array of pixels. Each pixel has an intensity value associated therewith that is related to the amount of x-ray energy that impinges on the pixel. During the data acquisition process, computer 100 receives the acquired projection data from data acquisition component 110 and stores the projection data at locations in a system memory device 112. The projection data is in the form of radiographs, or projection images. As such, cone beam projection data is acquired, wherein the data comprises a plurality of cone beam projection images.

In accordance with the present invention projection, a region of interest (ROI) of the object is identified within at least one of the projection images using a technique described below.

A region of interest (e.g., bone, organ, nodule, tumor, or other abnormality or the like) of the object may be identified by visualization by a technician or by using known automated detector techniques (e.g., algorithms to differentiate imaging representations of cancerous and normal tissue). Processing techniques exist that enable a projection image to be processed by a computer to identify particular features of interest. See, for example, Image-Processing Techniques for Tumor Detection, Robin N. Strickland, ed., Marcel Dekker, Inc., New York, 2002. Those skilled in the art will understand the manner in which such techniques can be employed. Other known processing techniques may be suitable for analyzing the projection image. The present invention is not limited with respect to the processing techniques that are described above.

When a particular region of interest is identified, a 3D lattice of points is constructed so that the projection of the points in the 3D lattice onto each selected projection image provides a sampling of the region of interest in the corresponding selected projection image. The constructed 3D lattice of points projects into regions (hereinafter called projection regions) of every acquired projection image. The projection data stored in memory device 112 that corresponds to the projection region of each projection image will be read out of memory device 112 and reconstructed using a reconstruction algorithm 114 in accordance with techniques known to those skilled in the art. Therefore, when the 3D lattice of the present invention is constructed with high resolution, the reconstructed image will have high resolution. Accordingly, the present invention enables reconstructing an arbitrary region of interest to a high resolution without requiring an initial reconstruction of the entire object. The reconstruction can then be displayed on a display device 116.

The cone beam CT system of the present invention includes a computer capable of being configured to perform the reconstruction algorithm of the present invention, and a memory device. It should be noted that it is not necessary that the computer and memory device that are used to perform the reconstruction algorithm 114 be computer 100 and memory device 112 that are utilized for the overall operations of the cone beam CT system. However, for ease of explanation, it will be assumed that the system of the present invention is comprised of computer 100 and memory device 112 of the cone beam CT system. Computer 100 can comprise one or more microprocessors, for example. The memory device comprised by the system of the present invention can be separate from the microprocessor(s) or it can be on-board memory contained on the microprocessor(s). Memory device 112 is not limited to any particular type of memory device. Preferably, the memory device is a solid state memory device, however it may also be, for example, a CD ROM, magnetic disk, magnetic tape, etc., or any other suitable computer-readable medium.

The method of the present invention in accordance with the preferred embodiment is generally described with reference to FIG. 2. At block 200, cone beam projection data is acquired. The acquired data is stored in memory 112 as a plurality of projection images available for use, if necessary, in reconstructing a high resolution image of a particular region of interest. At least one of the projection images is then selected, as indicated by block 202. A process technique is then performed to identify one or more regions of interest in the selected projection image, such as, for example, a lung nodule in a passageway of a human lung. This step, which is represented by block 204, can be performed automatically by a computer that performs, for example, a feature recognition routine, or it can be performed by a human (e.g., a technician or doctor). The selected projection image can be displayed on display device 116 to enable viewing by a human.

If a particular region of interest is identified, the projection data corresponding to the region of interest is available in memory device 112 to reconstruct a high resolution image of the region. The region of interest is either identified by a human/technician who uses an input device (e.g., a mouse, stylus, etc.) to identify the region of interest or by a computer that automatically identifies the region of interest. Once the region of interest has been identified, a three-dimensional lattice of points is defined, as indicated by block 206. The three-dimensional lattice of points is defined using a technique described below. Once the three-dimensional lattice of points has been defined, reconstruction is performed to generate an image of the region of interest of the object at each point in the lattice, as indicated by block 208.

Therefore, a single scanning procedure is used to acquire all of the data that is needed to perform the high resolution reconstruction. It should be noted that it is not necessary that the method of FIG. 2 be performed on-line while an object/patient 118 is being imaged. The method of the present invention may be performed entirely off-line. Though preferably, the method of the present invention is performed on-line in real time as patient 118 is being imaged. Alternatively, some of the steps may be performed on-line in real time and others may be performed off-line.

Figure 2:
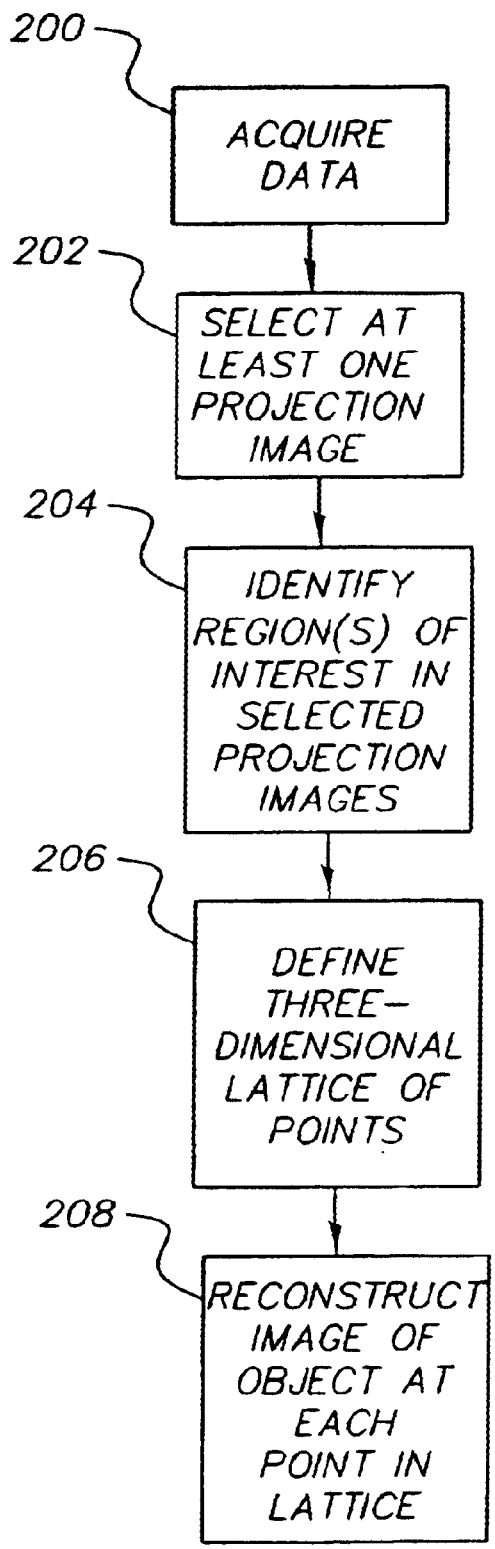
FIG. 2 shows a flow diagram of a method of reconstructing a three-dimensional image of a region of interest of an object from cone beam projection data in accordance with the present invention.
Figure 3A:
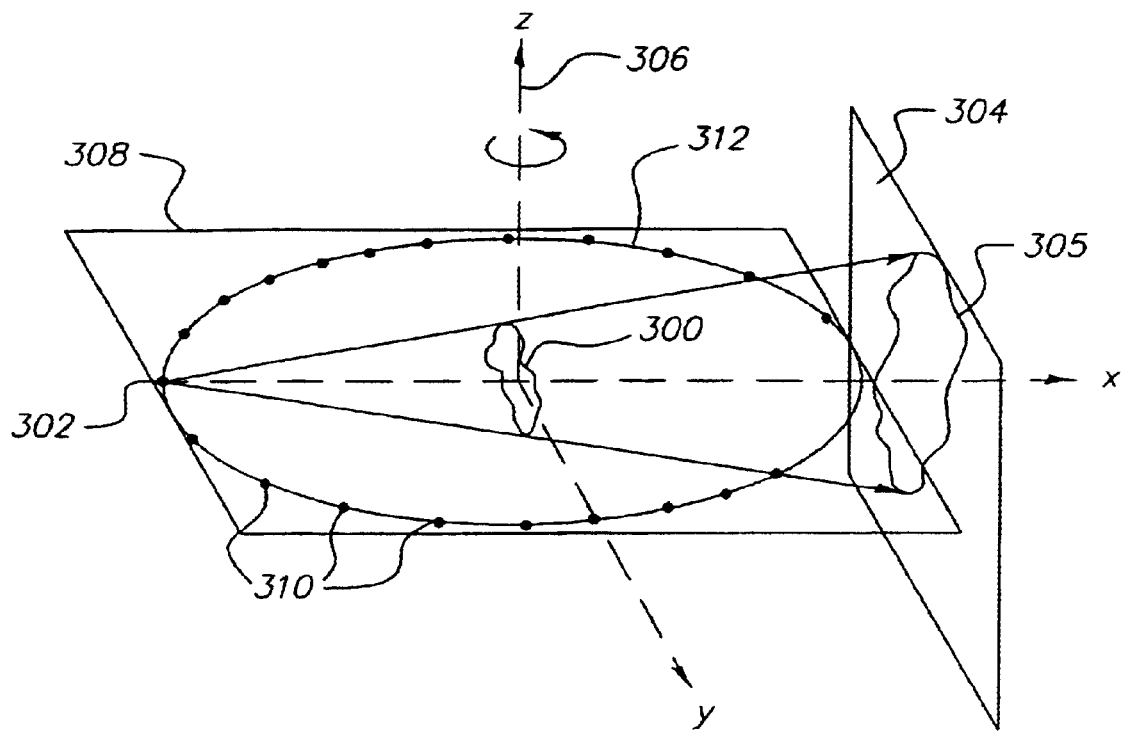
FIGS. 3a and 3b illustrate a cone beam scanning configuration for a first embodiment for performing specific steps of the present invention.
Figure 3B:
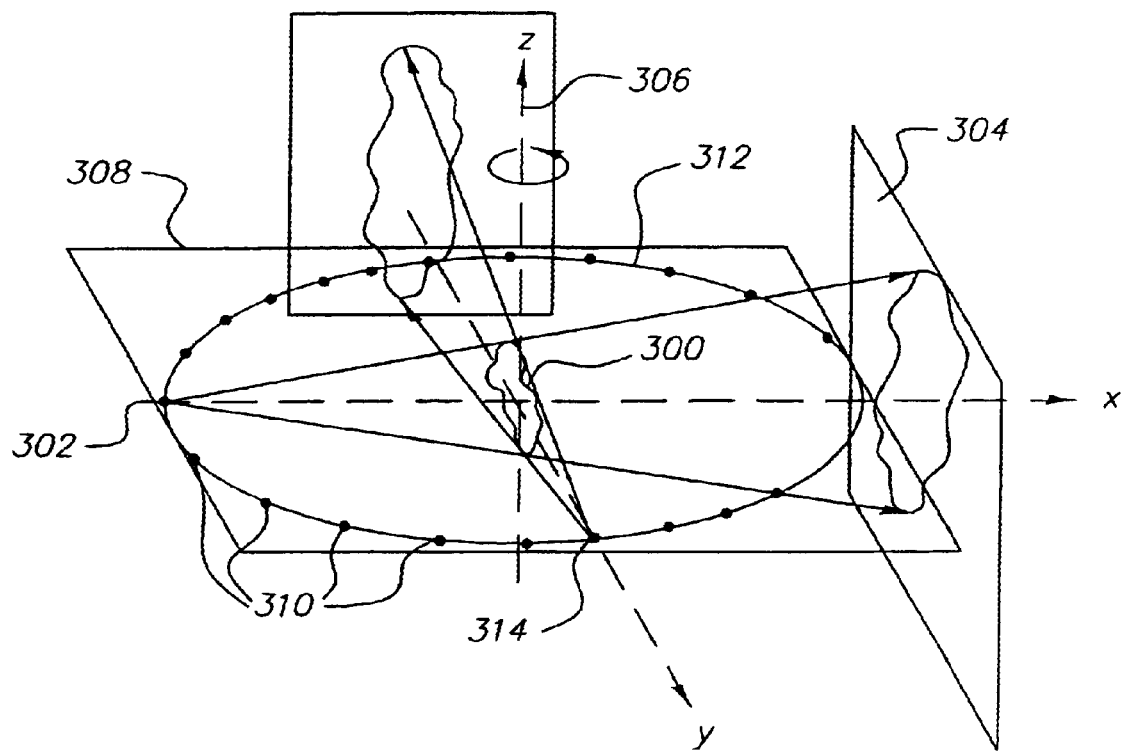

FIGS. 3a and 3b illustrate a first embodiment for performing the method shown in FIG. 2. Referring first to FIG. 3a, object 300 is positioned within a field of view between a cone beam x-ray source position 302 and a 2D detector array 304 whereby a cone beam projection image 305 is defined/recorded on array 304. An axis of rotation 306 (i.e., the z axis) passes through the field of view and object 300. For purposes of analysis, a midplane 308 is defined which contains the x-ray point source position 302 and is perpendicular to the axis of rotation 306. By convention, the axis of rotation 306 is referred to as the z-axis, and the intersection of the axis of rotation 306 and midplane 308 is taken as the origin of coordinates. As such, the x and y axes lie in midplane 308 as indicated, and the x,y,z coordinate system rotates with source position 302 and detector array 304. For imaging object 300 at a plurality of angular positions 310, source position 302 is moved relative to object 300 and the field of view along a circular trajectory 312 lying in midplane 308, while detector 304 remains fixed with respect to source position 302.

Once the plurality of projection images has been acquired, as indicated in block 202 of FIG. 2, at least one of the projection images that has been acquired to form the projection data is selected. In the preferred embodiment, exactly two projection images are selected. Preferably, those two projection images occur ninety (90) degrees apart along circular trajectory 312. FIG. 3b shows two x-ray source positions 302 and 314 which occur ninety degrees apart along circular trajectory 312. The reason for selecting two such projection images that are acquired ninety degrees apart will become apparent as will be described below. The selection can be automatic, for example, by automatically selecting the projection images corresponding to specific source positions, regardless of the content of the projection images at those source positions. Alternatively, the selection can be performed based on the content of the projection images, either by a human or by an automatic image processing method, so that one or both of the selected projection images have desired qualities. For example, if the object is a human chest, one of the selected projection images is chosen to be at the x-ray source position where the corresponding detector position is parallel to the coronal plane of the patient. If one of the selected projection images is chosen to have this property, it may be amenable to specialized automatic region of interest detection techniques that have been developed with respect to chest radiographs (see for example, B. van Ginneken, "Computer-Aided Diagnosis in Chest Radiography", Ph.D. Thesis, University Medical Center Utrecht, 2001).

A process technique (block 204 of FIG. 2) is performed to identify one or more regions of interest of the object in each selected projection image, such as, for example, a lung nodule in a passageway of a human lung. This step can be performed automatically by a computer that performs, for example, a feature recognition routine, or it can be performed by a human. The selected projection image may be displayed on display device 116 to enable viewing by a human. In the preferred embodiment, the process technique identifies the boundary of regions of interest in each selected projection image. In an alternative embodiment, the process technique identifies a containing boundary of regions of interest in each selected projection image. While the containing boundary can be of any shape/size, typically the containing boundary is usually chosen so that it has a simple shape, such as a circle, ellipse, or rectangle. If the process technique is performed by a human, identification of a containing boundary of each region of interest is generally much simpler and quicker than identifying the actual boundary of the region of interest, which may have intricate detail. For ease of illustration and discussion only, reference will be made to identifying the region of interest in each selected projection image with reference to a containing boundary.

Figure 4:
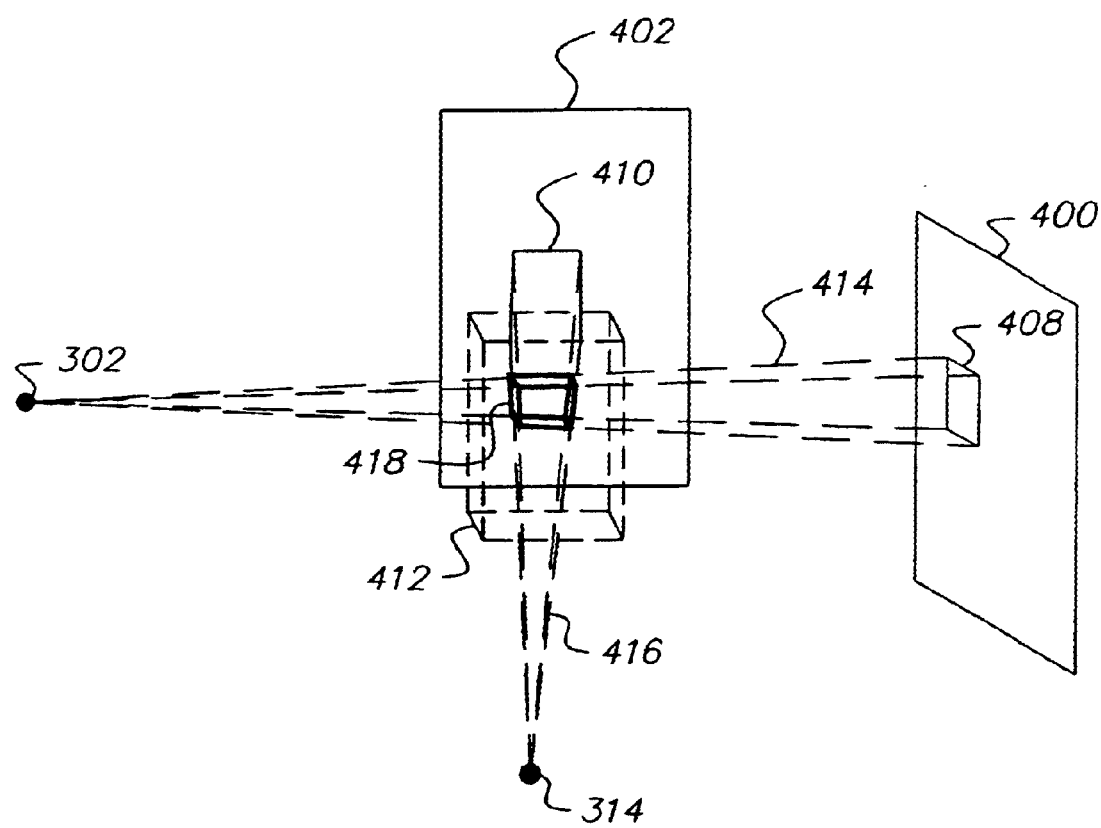
FIG. 4 illustrates a configuration for defining a three-dimensional lattice of points in accordance with a first embodiment of the present invention.

FIG. 4 illustrates a first embodiment for performing the step represented by block 206 in FIG. 2 using the configuration of FIGS. 3a and 3b. In this embodiment, exactly two projection images are selected. While any two projection images can be selected, preferably, those acquired at the indicated x-ray source positions 302 and 314 that occur ninety degrees apart along the circular trajectory 312 are selected. The two projection images are indicated by images 400 and 402, corresponding with x-ray source positions 302 and 314, respectively. Once the region of interest is identified, the region of interest is identified in each projection image 400,402. In FIG. 4, the region of interest projected on projection images 400,402 is indicated by boundaries 408 and 410, respectively. In a standard reconstruction procedure, all projection images would be used to reconstruct an image at each point in a lattice filling an entire three-dimensional volume, with boundaries indicated by a volume/region 412. In the present invention, however, boundaries 408 and 410 of the region of interest in projection images 400 and 402 are projected back to their respective x-ray source positions 302 and 314, respectively, to form projection cones 414 and 416. A volumetric region formed by the intersection of the interior of projection cone 414, the interior of projection cone 416, and the volume contained in volume 412 forms a reconstruction region 418. Volume 412, also referred to as object region 412, represents object 300, a portion of object 300, a region bounding all or portions of object 300, a volume which defines/represents object 300, a standard reconstruction region, or the like. Reconstruction region 418 is not as large as a standard reconstruction region (for example, the entire volume contained in volume 412) would be, and it contains the objects whose projection images lie within boundaries 408 and 410 of projection images 400 and 402, respectively.

A plurality of points, which will be referred to as a three-dimensional lattice of points, is then defined which form/outline reconstruction region 418. For example, a regular lattice containing 256×256×256 points (or 512×512× 512 points) sampling the circumscribing parallelepiped of reconstruction region 418 would provide a high resolution sampling of the reconstruction region. By defining the three-dimensional lattice this way, the region of interest can be reconstructed to a higher resolution than would be possible if the three-dimensional lattice sampled the entire volume contained within volume 412.

The volumetric boundary of a 3D region (i.e., reconstruction region 418) can be determined using techniques known to those skilled in the art. For example, the technique of back-projecting boundaries, and intersecting the volumetric back-projections in order to derive a volumetric boundary of a 3D object is well known in the art of three-dimensional object modeling systems. For example, see W. Martin and J. Aggarwal, "Volumetric Descriptions of Objects from Multiple Views," IEEE Trans. Pattern Analysis and Machine Intelligence, Vol. PAMI-5, No. 2, pp. 150–158, March 1983, and A. Laurentini, "The Visual Hull Concept for Silhouette-Based Image Understanding," IEEE Trans. Pattern Analysis and Machine Intelligence, Vol. 16, No. 2, pp. 150–162, February 1994.

The technique is extendable to a plurality of projection images. Indeed, using a higher number of images to derive a volumetric boundary of the three-dimensional object will yield a finer description of that volumetric boundary. However, in the context of cone beam CT reconstruction, selecting a high number of images increases the work required for identifying regions of interest in each selected image. Moreover, a coarse resolution of the volumetric boundary of the three-dimensional object ensures that the subsequent reconstruction will have high resolution in the areas of the region of interest.

The entire 3D density distribution can be reconstructed in an approximate sense from these projection images. A 3D reconstruction algorithm is described by L. A. Feldkamp, L. C. Davis, and J. W. Kress, in "Practical Cone-Beam Algorithm", *J. Opt. Soc. Am.* A, Vol. 1, No. 6, pp. 612–619, June 1984. Another reconstruction algorithm is disclosed in U.S. Pat. No. 5,270,926 (Tam). Additional information on 3D reconstruction algorithms is disclosed by A. C. Kak and M. Slaney, in *Principles of Computerized Tomographic Imaging*, (Classics in Applied Mathematics, SIAM, Philadephia, 2001), Chapter 3. Other 3D reconstruction algorithms/techniques may be known to those skilled in the art.

It is understood that more than two projection images can be selected. Selecting more than two projection images will allow for the subsequent lattice definition step, indicated by block 206 in FIG. 2, to be performed in a robust manner, however, it requires more work in the step of identifying regions of interest, indicated by block 204.

It is recognized that the entire volume 412 need not be employed; a portion of volume 412 can be employed. In a further embodiment, volume 412 is not employed. Rather, referring still to FIG. 4, the volumetric region of reconstruction region 418 is formed by the intersection of the interior of projection cone 414 and the interior of projection cone 416.

In an alternative embodiment, exactly one projection image can be selected, such as the projection image acquired at the indicated x-ray source position 302. Selecting one such projection image will allow for the subsequent lattice definition step (block 206) to be performed in a manner described with reference to FIG. 5.

Figure 5:
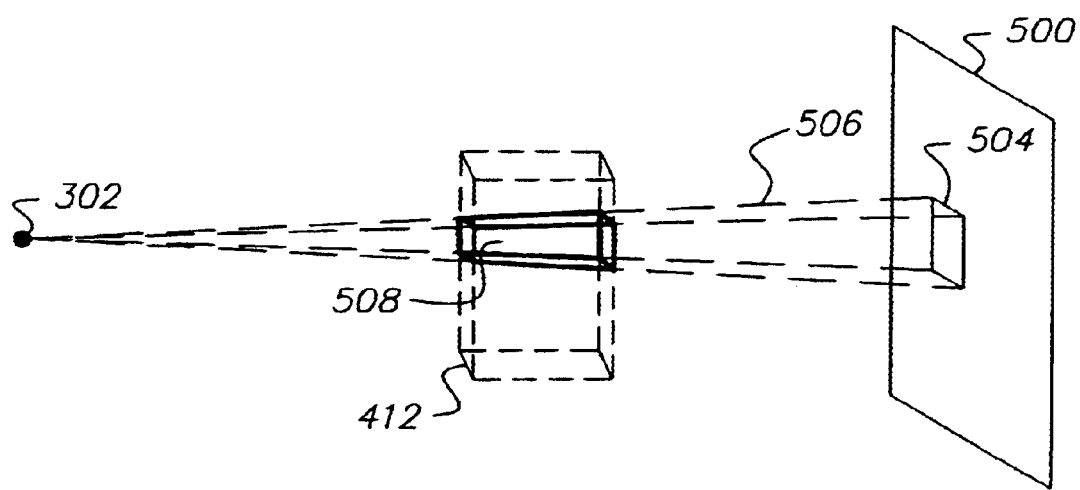
FIG. 5 illustrates a configuration for defining a three-dimensional lattice of points in accordance with another embodiment of the present invention.

FIG. 5 illustrates an alternative embodiment for performing the step represented by block 206 in FIG. 2. In this embodiment, exactly one projection image is selected, such as the one acquired at the indicated x-ray source position 302 in FIG. 3a. The projection image is indicated in FIG. 5 as projection image 500, and the corresponding x-ray source position by source position 302. The identified region of interest in projection image 500 is indicated by boundary 504. Boundary 504 of the region of interest in projection image 500 is projected back to its x-ray source point 302, forming projection cone 506. A volumetric region is formed by the intersection of the interior of projection cone 506 and the volume contained in volume 412; the formed volumetric region being defined as reconstruction region 508. Reconstruction region 508 is not as large as a standard reconstruction region (for example, the entire volume contained in volume 412) would be, and it contains the object whose projection images lie within boundary 504 of projection image 500. As compared to the previous embodiment described in FIG. 4, reconstruction region 508 is clearly larger than reconstruction region 418 because there is not a second region of interest from a second image contributing to the location of the reconstruction region; however, the benefit of this embodiment is that only one boundary needs to be located in one projection image. A three-dimensional lattice of points is then defined to define/contain reconstruction region 508. For example, a regular lattice containing 256×256×256 points (or 512×512×512 points) sampling the circumscribing parallelepiped of reconstruction region 508 would provide a high resolution sampling of the reconstruction region. By defining the three-dimensional lattice this way, the region of interest can be reconstructed to a higher resolution than would be possible if the three-dimensional lattice sampled the entire volume contained within volume 412.

Figure 6:
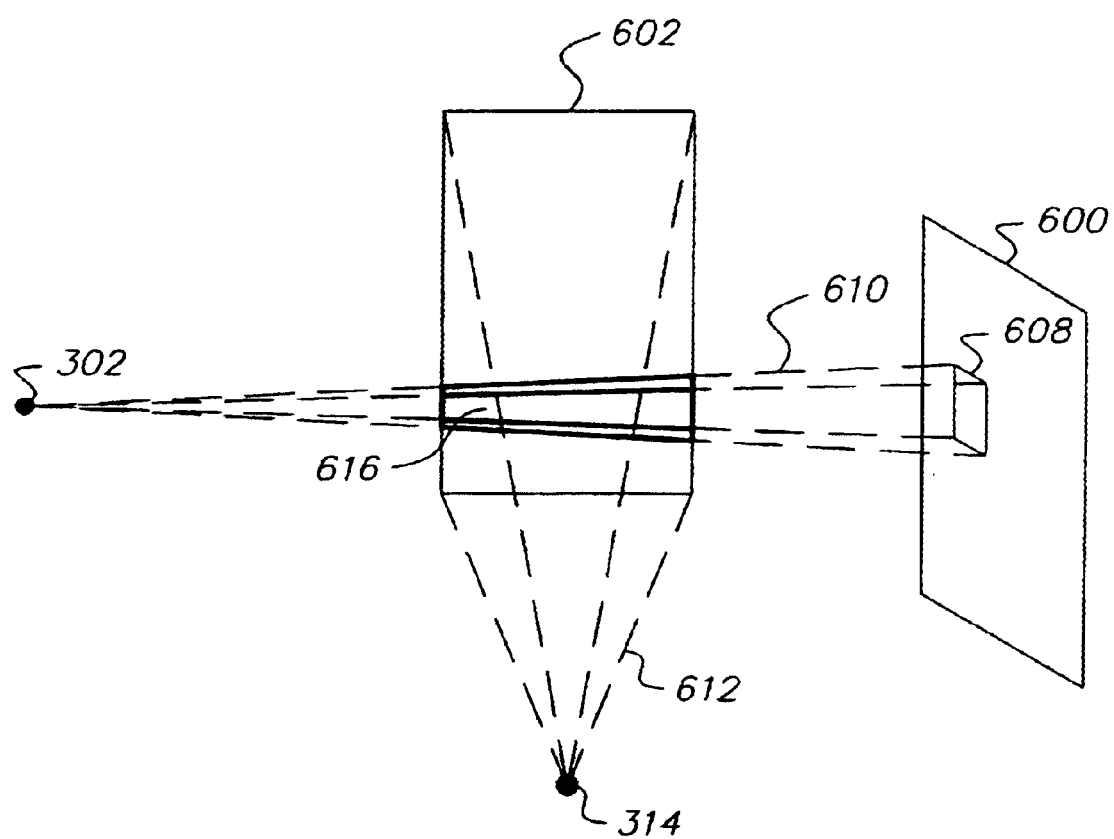
FIG. 6 illustrates a configuration for defining a three-dimensional lattice of points in accordance with a further embodiment of the present invention.

FIG. 6 illustrates a further embodiment for performing the step represented by block 206 in FIG. 2. In this embodiment, at least two projection images are selected, however, volume 412 is not employed and the region of interest is only identified on one projection image. Any two projection images can be selected, though preferably, two projection images that occur ninety degrees apart along circular trajectory 312 are selected. As illustrated in FIG. 6, two projection images 600 and 602 correspond with source positions 302 and 314, respectively. The identified region of interest is projected onto projection image 600, indicated in FIG. 6 as boundary 608. Boundary 608 is projected back to source position 302 thereby forming projection cone 610. However, the identified region of interest is not projected onto projection image 602 to define a boundary. Rather, the complete projection image 602 is projected back to its source position 314, thereby forming projection cone 612. As such, only one boundary is defined and projected. A reconstruction region 616 is formed by the intersection of the interior of projection cones 610 and 612. Note that volume 412 was not employed in this embodiment. Reconstruction region 616 is not as large as a standard reconstruction region would be, and it contains the objects whose projection images lie within containing boundary 608 of projection image 600. A three-dimensional lattice of points is then defined to define/contain reconstruction region 616. For example, a regular lattice containing 256×256×256 points (or 512×512×512 points) sampling the circumscribing parallelepiped of reconstruction region 616 would provide a high resolution sampling of the reconstruction region.

It is understood that the present invention is not limited to any particular computer for performing the data acquisition and processing tasks of the present invention. The term "computer", as that term is used herein, is intended to denote any machine/processor capable of performing the calculations, or computations, necessary to perform the tasks of the present invention. Therefore, the computer utilized to perform reconstruction algorithm 114 of the present invention may be any machine that is capable of performing the necessary tasks.

A number of CT reconstruction algorithms are suitable for computing the reconstruction. The CT reconstruction algorithm 114 utilized for this purpose can be a known CT reconstruction algorithm or a proprietary CT reconstruction algorithm. The well known aforementioned Feldkamp algorithm is suitable for these purposes. Exact cone beam reconstruction algorithms are also suitable for this purpose. The present invention is not limited with respect to the reconstruction algorithm that is utilized for this purpose.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

100 computer
102 x-ray source
104 detector
106 controller
108 controller
110 data acquisition component
112 system memory
114 reconstruction algorithm
116 display device
118 patient
200 acquire data step
202 select projection image step
204 identify region of interest step
206 define three-dimensional lattice step
208 reconstruct image step
300 object
302 x-ray source position
304 detector array
305 cone beam projection image
306 axis of rotation
308 midplane
310 x-ray source positions
312 circular trajectory
314 x-ray source position
400 projection image
402 projection image
408 region of interest; boundary
410 region of interest; boundary
412 volume; object region; standard reconstruction region
414 projection cone
416 projection cone
418 reconstruction region
500 projection image
504 region of interest; boundary
506 projection cone
508 reconstruction region
600 projection image
602 projection image
608 region of interest; boundary
610 projection cone
612 projection cone
616 reconstruction region

What is claimed is:

1. A method for reconstructing a three-dimensional image of an object from cone beam projection data, the method comprising the steps of:

acquiring the cone beam projection data, the cone beam projection data comprising a plurality of cone beam projection images;

determining a three-dimensional reconstruction region using a region of interest identified in at least one of the plurality of cone beam projection images, the three-dimensional reconstruction region being defined by a plurality of points; and reconstructing the image at each of the plurality of points to form the three-dimensional image of the region of interest.

2. The method of claim 1, wherein the step of determining comprises the steps of:

identifying the region of interest within at least two of the plurality of projection images; and projecting each identified region of interest through at least a portion of the object to identify the three-dimensional reconstruction region.

3. The method of claim 1, wherein the cone beam projection data is acquired by operating a source and a detector arrangement at a plurality of source positions along a scan path that encircles the region of interest of the object.

4. The method of claim 1, wherein a source and detector arrangement rotate about an axis of rotation and the projection images are acquired at angular increments about the axis of rotation, the step of identifying the regions of interest comprises the steps of:

selecting, from the plurality of projection images, a first projection image at a predetermined angle; and selecting, from the plurality of projection images, a second projection image at an angle ninety degrees beyond the predetermined angle.

5. The method of claim 1, wherein the step of determining comprises the steps of:

identifying a region of interest within a plurality of projection images;

projecting each identified region of interest to a source position corresponding with the associated projection image to define a three-dimensional projected cone; and sampling the intersection of the projected cones to determine a three-dimensional reconstruction region defined by a plurality of points.

6. The method of claim 5, wherein the step of identifying a region of interest comprises the step of identifying regions of interest with two cone projection images disposed at ninety degrees from each other.

7. The method of claim 1, wherein the step of determining comprises the steps of:

identifying the region of interest within one of the plurality of projection images; and projecting the identified region of interest through at least a portion of the object region to fine the three-dimensional reconstruction region.

8. The method of claim 1, wherein the step of determining comprises the steps of:

identifying a region of interest within a first one of the plurality of projection images;

projecting the identified region of interest to a source position corresponding with the first one of the plurality of projection images to define a first three-dimensional projection cone;

projecting a second one of the plurality of projection images to a source position corresponding with the second one of the plurality of projection images to define a second three-dimensional projection cone; and using the first and second projected cones to determine a three-dimensional reconstruction region defined by a plurality of points.

9. A computer storage product having at least one computer storage medium having instructions stored therein causing one or more computers to perform the method of claim 1.

* * * * *